United States Patent [19]

Upsher

[11] Patent Number: 4,930,495

[45] Date of Patent: Jun. 5, 1990

[54] LARYNGOSCOPE INCLUDING A DISPOSABLE BLADE AND ITS METHOD OF USE

[75] Inventor: Michael S. Upsher, San Mateo, Calif.

[73] Assignee: The Upsher Laryngoscope Corporation, Burlingame, Calif.

[21] Appl. No.: 282,115

[22] Filed: Dec. 9, 1988

[51] Int. Cl.⁵ .............................................. A61B 1/26
[52] U.S. Cl. .......................................... 128/10; 128/3
[58] Field of Search ............................ 128/3, 4, 9–11, 128/15, 17, 18, DIG. 12, 303 R, 200.26; 604/110

[56] References Cited

U.S. PATENT DOCUMENTS

| | | | |
|---|---|---|---|
| 3,878,836 | 4/1975 | Twatler | 128/9 |
| 4,406,280 | 9/1983 | Upsher | 128/11 |
| 4,557,256 | 12/1985 | Baumam | 128/11 |
| 4,775,364 | 10/1988 | Alles | 604/110 |
| 4,808,167 | 2/1989 | Mamm et al. | 128/DIG. 12 |

*Primary Examiner*—Edward M. Coven
*Assistant Examiner*—Mark S. Graham
*Attorney, Agent, or Firm*—Flehr, Hohbach, Test, Albritton & Herbert

[57] ABSTRACT

A laryngoscope is disclosed herein which includes a handle and a separate disposable blade. The disposable blade is designed for a single proper operative use, enabling greater sterility. After the single first proper operative use, and upon disengagement from the handle, certain blade components are sufficiently damaged, whereby the blade is not able to cooperatively engage and remain retained in the handle, for a proper second operative use.

6 Claims, 2 Drawing Sheets

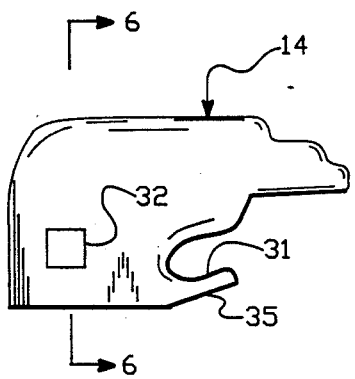
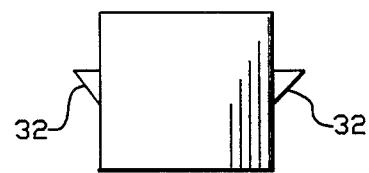
FIG.-5  FIG.-6
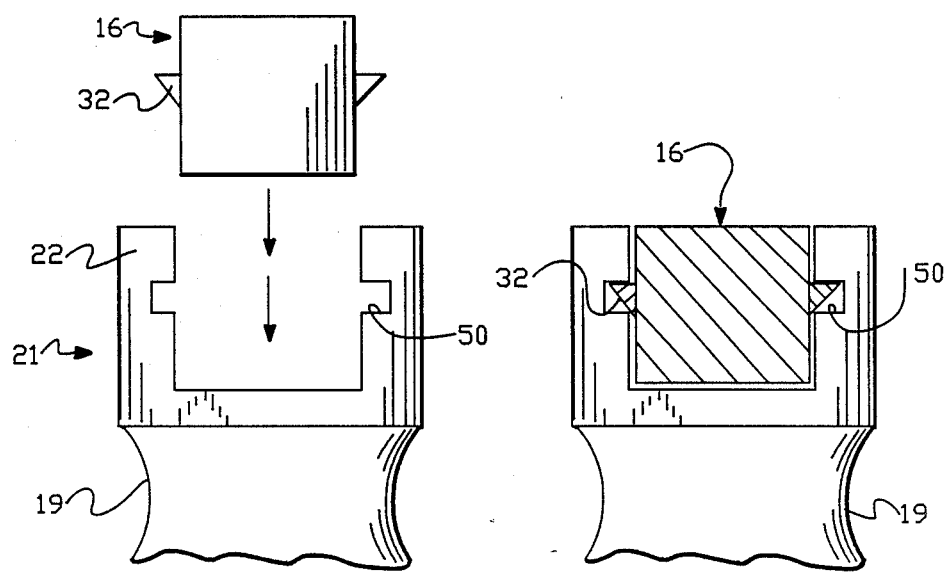
FIG.-7  FIG.-8

LARYNGOSCOPE INCLUDING A DISPOSABLE BLADE AND ITS METHOD OF USE

The present invention relates generally to a laryngoscope and more particularly to a laryngoscope which utilizes a specifically designed disposable blade.

There are presently a number of generally similar types of laryngoscopes available in the prior art. A typical laryngoscope available includes an elongated handle, a separate blade for use on the handle, and an arrangement carried partially by the handle and partially by the blade for producing a beam of light in a predetermined direction relative to the blade.

While laryngoscopes of the type described are generally satisfactory for their intended use, Applicant has found that the continued use of the same laryngoscope blade (1) requires sterilization which can be a costly procedure and (2) can result in cross-infection between patients. Accordingly, a primary object of the present invention is to provide a laryngoscope including a blade which is specifically designed to be disposable.

Another object of the present invention is to provide a disposable laryngoscope blade which is economical to manufacture and reliable to use.

Still another object of the present invention is to provide a disposable laryngoscope blade and associated handle having means which are designed to cooperate with one another so as to specifically discourage use of the blade more than once, but without interfering with its proper use the first time.

In accordance with an actual working embodiment of the present invention, the cooperating means recited above are formed by frangible tabs protruding out on opposite sides of the blade and recesses provided on opposite sides of the handle, for receiving the tabs. This cooperating arrangement of tabs and recesses not only causes the blade to be retained in the handle for a first operative use but causes a component of the blade, specifically, the tab, to be damaged sufficient to discourage use of the blade a second time without preventing it from being used in the proper way the first time.

The laryngoscope disclosed herein, and particularly its arrangement of tabs and recesses, will be discussed in detail hereinafter in conjunction with the drawings, wherein:

FIG. 5 is a side view of the blade, specifically, the handle connecting segment;

FIG. 6 is a cross-sectional view of the handle connecting segment of the blade shown in FIG. 5, taken along line 6—6;

FIG. 7 is a rear view of the blade (handle connecting segment) immediately prior to attachment with the handle (blade attaching head portion);

FIG. 8 is a rear view of the blade (handle connecting segment) within the handle (blade attaching head portion).

Figure 1:
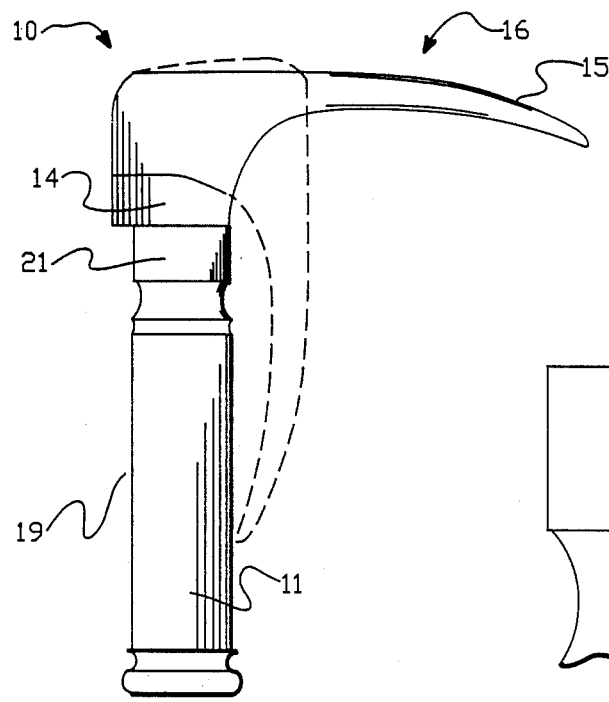
FIG. 1 is a side elevational view of a laryngoscope designed in accordance with the present invention and including a handle and blade, the latter being shown by solid lines in an operative position and by dotted lines in an inoperative position with respect to the handle.

Turning now to the drawings, wherein the components are designated by like reference numerals throughout the various figures, attention is first directed to FIG. 1. The laryngoscope 10 comprises two members, a handle 19 and a disposable blade 16, mounted to said handle 19 for movement between an operative position, shown in solid lines, and an inoperative position, shown in phantom.

Overall, laryngoscope 10 may be identical to the laryngoscope described in U.S. Pat. No. 4,406,280, except for the way in which the blade 16 is made disposable. For this reason, U.S. Pat. No. 4,406,280 is incorporated herein by reference.

Figure 2:
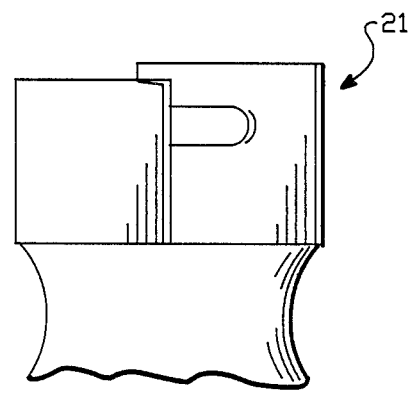
FIG. 2 is a skewed front view of the blade attaching head portion of the handle.

Returning to FIG. 1, the handle 19 may be functionally divided into two portions, a hand gripping portion 11 and a blade attaching head portion 21. The blade attaching head portion 21, shown best in FIGS. 2-4, includes means for receiving and retaining the blade for a first operative use. The handle 19 is preferably made of stainless steel, although other suitable materials include metals, plastic or the like.

The blade 16 which removably attaches to the handle 19 may be functionally divided into two segments, a handle connecting segment 14 and a tongue holding segment 15. The handle connecting segment 14, mounts to the blade attaching head portion 21 of the handle 19. On the blade attaching head portion of the handle 21 are means for attaching and retaining the blade 16. Throughout use, the attaching means on both the blade 16 and the handle 19 remain intact. However, the cooperating retaining means on the handle connecting portion of the blade 14 are damaged so as to discourage a second operative use of the blade 16, as will be seen hereinafter. Extending frontward from the handle connecting segment of the blade 14 is the tongue holding segment 15.

This blade 16 is integrally constructed and is preferably disposable. The preferred blade is made of plastic, but other suitable materials such as metals may be used.

Figure 3:
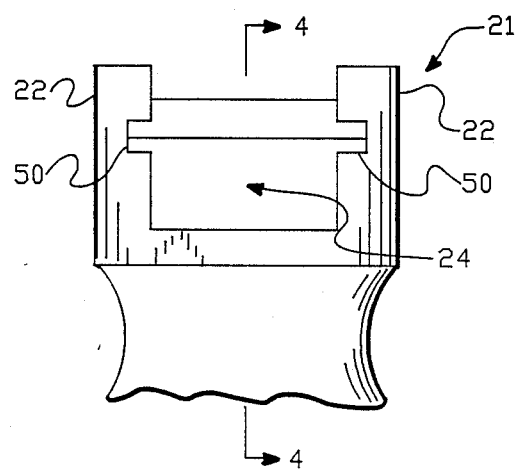
FIG. 3 is a rear view of the blade attaching head portion of the handle.

FIG. 3 is a partial side view of the blade attaching portion of the handle 21. Two parallel upright structures 22 form the top of the blade attaching head portion 21. A perpendicular crossbar pin 20 extends between the upright structures 22. The blade pivotally attaches to the handle 19 at this blade attaching portion 21, about the crossbar pin 20, in the space 24 between the upright structures 22.

Figure 4:
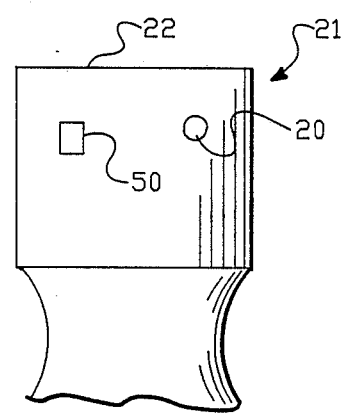
FIG. 4 is a cross-sectional view of the blade attaching head portion of the handle, shown in FIG. 3, taken along line 4—4.

FIG. 4 is a cross section along line 4—4 of FIG. 3. This figure shows the inner surface of one of the upright structures 22 of the blade attaching head portion of the handle 21. The crossbar pin 20 is closest to the front. Proximate to the crossbar pin 20 are recesses 50 which cooperate with means on the blade 16 for retaining the blade 16 within the handle 19 for a first operative use. These recesses 50 also function to damage the blade upon completion of a first operative use when force thereafter is applied to the blade 16 moving it to an inoperative position. Crossbar pin 20 should preferably be located as far front as possible for pivotal blade attachment. Recesses 50 may be anywhere along the inside sides of the upright structures 22 of the blade attaching head portion of the handle 21.

FIG. 5 is a side view of the handle connecting segment of the blade. The blade illustrated consists of this segment and the previously recited curved tongue holding segment 15, which is shown in FIG. 1. While a curved tongue holding segment is preferred, this segment can have a multitude of shapes such as rectangular. The tongue holding segment 15 suppresses the tongue, placing it against the oral cavity floor. This maximizes the free space in the oral cavity, providing the health professional with an unobstructed view of the patient's throat, enabling easier intubation.

Rearward from the tongue holding segment 15 is the handle connecting segment 14. This handle connecting segment 14 comprises a jaw 35 including a slot 31 designed for pivotal engagement with the crossbar pin 20. This design enables a secure engagement during the first proper operative use. Additionally, in accordance with the present invention, the handle connecting segment of the blade 14 comprises protruding frangible tabs 32, which cooperate with the recesses 50 in the blade attaching head portion of the handle 21 for retaining the blade in a first operative position as will be seen hereinafter with respect to FIGS. 7 and 8. The protruding frangible tabs 32 can be of any shape and located anywhere on the opposite outside sides of the handle connecting segment of the blade 14 so long as they cooperatingly fit within the recesses 50 of the blade attaching portion of the handle 21 (see FIG. 4) and break away from the rest of the blade 16 in the manner to be described. Triangular tabs are preferred since they easily snap into place and are not damaged upon downward blade attachment and engagement, prior to a first proper operative use, as best seen in FIGS. 7 and 8. However, as the blade 16 is pivoted downward after its first use, with sufficient force, the tabs 32 will break off in order to accommodate this pivotal movement. This is because there is no other way to remove the blade 16. Note specifically in FIG. 8, the flat upper surfaces of the tabs engage the upper flat surfaces of recesses 50. Preferably, these tabs 32 are integrally formed of plastic along with the rest of the blade 16. Thus, the tabs 32 are such that they can withstand a first attachment and cooperative engagement with the respective recesses 50 on the blade attaching portion of the handle 21, providing sufficient retentive force for a first proper operation of the blade 16. However, the tabs 32 are configured to break within the recesses 50 when the blade is 16 is forcibly removed from the handle 19. Additionally, while two frangible tabs 32 (one on each side of the handle connecting segment of the blade 14) are preferred, the laryngoscope can function with as few as one frangible tab and cooperating recess, provided this arrangement yields a retaining force sufficient for a proper first time operative use. Any number of additional frangible tabs may be added, provided there is a correspondingly cooperating recess for each tab.

FIG. 7 is a rear view of the blade as it moves downward for attachment to the handle, for a first time. The protruding frangible tabs 32 of the blade 16 are forced by a cam like action into the recesses 50 of the handle's upright structures 22. Pin 20 of the blade attaching head portion of the handle 21 has been omitted for purposes of clarity.

FIG. 8 shows the identical rear view as FIG. 7, but the tabs 32 of the blade 16 are in place within the recesses 50 of the handle 19.

Having now described laryngoscope blade 16 and handle 19 in their entirety from a structural standpoint, attention is directed to the way in which the blade 16 is connected and interacts with the handle 19, as illustrated by the drawing figures. Initially, the blade 16 and the handle 19 are separate pieces. When a proper first operative use of the laryngoscope 10 is desired, the health professional will attach the blade 16 to the handle 19, engaging the blade slot 31 with the crossbar pin 20 of the handle 19. Initial attachment to a first inoperative position is complete when the blade 16 has been pulled as far forward as possible and the curved portion of the slot 31 pivotally engages the crossbar pin 20 of the handle 19.

Upon initial attachment to a first inoperative position, the health professional will now push up on the tongue holding segment of the blade 15 until the blade is firmly retained in the handle 19. Retention is maintained by protruding frangible tabs 32 on the blade which cooperate with recesses 50 in the blade attaching head portion of the handle 21. Once the blade 16 is firmly retained in the handle 19, the first operative position is achieved. The health professional may now use the laryngoscope 10 properly for a first and only operative use.

When this first operative use is complete, the health professional will disengage the blade 16 from the handle 19. The disengagement process will occur in such a way as to damage the blade 16 discouraging a second operative use.

Disengagement begins when downward force is applied to the blade 16, sufficient to overcome the blade retentive force. Upon movement out of the recesses 50 of the handle 19, the frangible tabs 32 are damaged whereby they are broken off of the blade, sufficiently deformed, or sufficiently weakened. Reduced to remnants, the frangible tabs 32 will no longer fit within the recesses 50 and provide sufficient retentive force for the blade 16. Thus, the damaged blade 16 can not be retained in the handle 19 for a proper second operative use.

The damaged blade is now in an inoperative position and can be finally disconnected from the handle 19. Disconnection is achieved by pushing the damaged blade, now in a second inoperative position, rearward, whereby the slot 31 no longer communicates with the crossbar pin 20. The disconnected blade can now be disposed of. A new sterile blade may now be attached for use by the above described method.

What is claimed is:

1. A laryngoscope, comprising:
   (a) a handle;
   (b) a disposable blade separate from said handle;
   (c) means forming part of said handle and part of said blade for supporting the blade to said handle for movement between an operative position and an inoperative position, said supporting means including a blade attaching head portion of said handle and a handle connecting segment of said blade; and
   (d) means for retaining said blade in its operative position after the blade has been placed in that position for the first use, said retaining means including at least one component thereof which is adapted to be damaged as a result of said first use to a degree sufficient to prevent said retaining means from reliably retaining said blade in its operative position a second time, said retaining means including at least one recess in said blade attaching head portion and a frangible projection in said handle connecting end segment of said blade, said frangible projection serving as said one component of said retaining means.

2. The laryngoscope of claim 1, in which said blade attaching head portion of said handle contains a crossbar pin means for pivotally attaching said head portion of said handle to a corresponding slot in said handle connecting segment of said blade, allowing said blade to pivotally move between operative and inoperative positions.

3. The laryngoscope of claim 1, wherein said head portion includes a crossbar and wherein said handle connecting segment includes a crossbar slot.

4. A laryngoscope comprising:
 (a) a handle;
 (b) a blade separate from said handle;
 (c) cooperating retaining means on said handle and said blade at a point where said handle attaches to said blade for retaining said blade in an operative position after the blade has been placed in an operative position for a first use and for damaging said retaining means on said blade upon movement of said blade to an inoperative position after a first operative use, whereby to damage the retaining means to a sufficient degree so as to discourage a second operative use upon movement from the first operative position, said cooperating retaining means comprising at least one recess located on said handle and at least one frangible tab located on said blade, said frangible tab being designed to break when moved out of the operative position for the first time.

5. The laryngoscope of claim 4, wherein said handle contains a crossbar pin at one end, and wherein said blade includes a crossbar slot at one end, for attaching said blade to said handle.

6. The laryngoscope of claim 5, wherein said crossbar pin attaches said handle to said blade in a pivoting manner, for movement of said blade between operative and inoperative positions.

* * * * *